United States Patent [19]

Harada et al.

[11] 4,370,502
[45] Jan. 25, 1983

[54] PROCESS FOR PRODUCING P-NITROANILINE

[75] Inventors: Taira Harada, Mitaka; Toyozi Shimizu, Iwakuni; Takenori Nagaoka, Tokyo, all of Japan

[73] Assignee: Mitsui Petrochemical Industries Ltd., Tokyo, Japan

[21] Appl. No.: 243,496

[22] Filed: Mar. 13, 1981

[30] Foreign Application Priority Data

Mar. 17, 1980 [JP] Japan ................... 55-32626

[51] Int. Cl.³ ............... C07C 85/24; C07C 87/60; C07C 119/10
[52] U.S. Cl. ................... 564/411; 564/273; 564/275; 564/441
[58] Field of Search .................. 564/411, 441

[56] References Cited

U.S. PATENT DOCUMENTS

| | | | |
|---|---|---|---|
| 3,641,154 | 2/1972 | Corbett et al. | 564/411 |
| 3,714,272 | 1/1973 | Coon et al. | 568/934 |

FOREIGN PATENT DOCUMENTS

| | | | |
|---|---|---|---|
| 72173 | 11/1892 | Fed. Rep. of Germany | 564/411 |
| 52-136134 | 11/1977 | Japan | 564/411 |

*Primary Examiner*—John Doll
*Attorney, Agent, or Firm*—Sherman & Shalloway

[57] ABSTRACT

A process for producing p-nitroaniline, which comprises nitrating an α-methylbenzalaniline of the formula

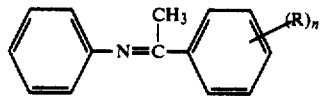

wherein R represents an alkyl group having 1 to 5 carbon atoms, and n is 0 or 1,
with nitric acid in the presence of a halogenated aliphatic hydrocarbon solvent and sulfuric acid to form a p-nitro-α-methylbenzalaniline of the formula

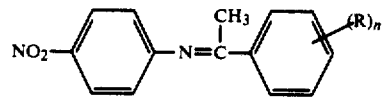

wherein R and n are as defined above,
and hydrolyzing the p-nitro-α-methylbenzalaniline.

7 Claims, No Drawings

PROCESS FOR PRODUCING P-NITROANILINE

This invention relates to an improved process by which p-nitroaniline can be produced selectively in high yields at low cost with commercial advantage from a raw material that is less expensive and more readily available commercially than in the prior art.

More specifically, this invention pertains to a process for producing p-nitroaniline, which comprises nitrating an α-methylbenzalaniline of the following formula (III)

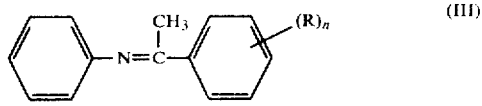

wherein R represents an alkyl group having 1 to 5 carbon atoms, and n is 0 or 1,
with nitric acid in the presence of a halogenated aliphatic hydrocarbon solvent and sulfuric acid to form a p-nitro-α-methylbenzalaniline of the following formula (II)

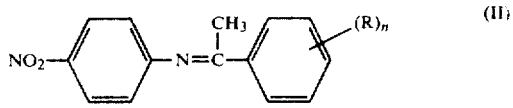

wherein R and n are as defined,
and hydrolyzing the resulting p-nitro-α-methylbenzalaniline.

p-Nitroaniline is utilized as a manufacturing intermediate for dyes, agricultural chemicals, pharmaceuticals, etc., and p-phenylenediamine obtained by reduction of p-nitroaniline is useful as a manufacturing intermediate for polyamides, rubber compounding agents, synthetic resin additives, dyes, pharmaceuticals, agricultural chemicals, etc. Hence, an increased demand for p-nitroaniline as an industrial material is expected.

According to the prior art, p-nitroaniline is produced, for example, by a method which comprises reacting a p-halonitrobenzene such as p-chloronitrobenzene with ammonia, or a method which comprises nitrating acetanilide and hydrolyzing the reaction product. In the former method, however, the starting p-chloronitrobenzene is difficult to produce in high yields with good selectivity. The latter method also has the disadvantage that in the hydrolysis of the p-nitroacetanilide an equimolar amount, to the p-nitroacetanilide, of alkali is required, and acetic acid formed as a by-product of the hydrolysis is difficult to recover. Because of such difficulties and disadvantages, these conventional methods for producing p-nitroaniline are industrially unsuitable.

German Patent Specification No. 72173 discloses a method for producing an aromatic primary monoamine, such as p-nitroaniline, which comprises nitrating a benzalaniline (benzylideneaniline) which may be represented by the following formula

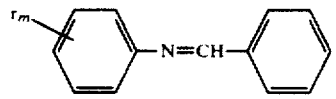

wherein r represents a methyl or methoxy group and m is 0, 1 or 2,
with nitric acid in sulfuric acid, and then hydrolyzing the resulting product. Example 1 of this patent document states that p-nitroaniline was obtained in a yield of 90% from benzalaniline. The German patent, however, does not at all refer to the use of an α-substituted compound of benzalaniline including the α-methylbenzalaniline represented by formula (III) given hereinabove. Furthermore, it is completely silent on the use of solvents other than sulfuric acid in the nitration reaction. The starting benzalaniline used in this patent can be obtained by condensation between benzaldehyde and aniline. Benzaldehyde, however, is not available at low cost because it is chemically unstable and its production requires a complex process and is costly. Hence, the starting benzalaniline is unsatisfactory for industrial production of p-nitroaniline at low cost.

Japanese Laid-Open Patent Publication No. 136,134/1977 discloses a method for producing p-phenylenediamine, which comprises nitrating benzalaniline with nitric acid and trifluoromethanesulfonic acid, diluting the reaction product with water to hydrolyze it to p-nitroaniline, isolating it, and reducing it.

This Japanese patent document neither refers at all to the use of the α-substitution product including the α-methylbenzalaniline of formula (III). The nitrating agent used in this patent document consisting of nitric acid and trifluoromethanesulfonic acid is disclosed in U.S. Pat. No. 3,714,272. The Japanese document states that the ratio between the o-isomer and the p-isomer obtained by the nitration reaction varies greatly depending upon the type of compound to be reacted and the reaction conditions, and cannot be anticipated simply by the yields of the nitrated product. As support for this statement, the specification describes that in the nitration of acetanilide, no substantial difference in the increasing of the yield of p-isomers is noted between the use of nitric acid and sulfuric acid as a nitrating agent and the use of nitric acid and trifluoromethanesulfonic acid as a nitrating agent, but that in the nitration of benzalaniline, the use of nitric acid and trifluoromethanesulfonic acid results in almost complete inhibition of the formation of the o-isomer and therefore in a marked increase in the yield of the p-isomer. On this basis, the Japanese patent document specifies the use of benzalaniline as a starting material. The use of benzalaniline, however, causes the same cost problem as described above with regard to German Pat. No. 72173. Furthermore, the proportion of trifluoromethanesulfonic acid as a nitrating reagent is at least 1 mole, preferably at least 2 moles, per mole of benzalaniline, and in working examples, the amount is the one which is sufficient for it to act also as a solvent. Since trifluoromethanesulfonic acid is expensive, the cost problem mentioned above cannot still be solved in commercial practice.

The present inventors have made extensive investigations in order to develop an improved process by which p-nitroaniline can be produced in high yields selectively at low cost with commercial advantage from a material that is less expensive and more readily available commercially than in the prior art.

These investigations have led to the discovery that by nitrating the α-methylbenzalaniline of formula (III) with nitric acid in the presence of a halogenated aliphatic hydrocarbon solvent and sulfuric acid to form the compound of formula (II) given hereinabove and hydrolyzing the compound (II), p-nitroaniline can be produced in a surprisingly increased yield of about 99% or more with good selectivity, and the amounts of o- and m-isomers can be reduced to a negligible extent.

This process has also been found to be industrially beneficial in that the starting α-methylbenzalaniline of formula (III) is commercially available at a lower cost and with greater ease than benzalaniline, the nitrating agent used is less expensive than the reagent used in the aforesaid prior art which consists of nitric acid and trifluoromethanesulfonic acid, and acetophenone formed as a by-product in the hydrolyzing step can be recycled for the production of the starting compound of formula (III).

It is an object of this invention therefore to provide an improved process for industrially producing p-nitroaniline.

The above and other objects and advantages of this invention will become more apparent from the following description.

The α-methylbenzalaniline of the formula

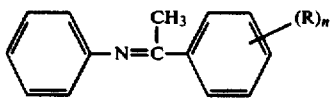

(III)

wherein R represents an alkyl group having 1 to 5 carbon atoms, preferably 1 to 3 carbon atoms, and n is 0 or 1, can be produced easily in high yields and at low costs by condensation reaction between aniline and acetophenone or an alkylacetophenone of formula (IV) below (in which R and n are as defined with regard to formula (III)) in accordance with the following reaction scheme.

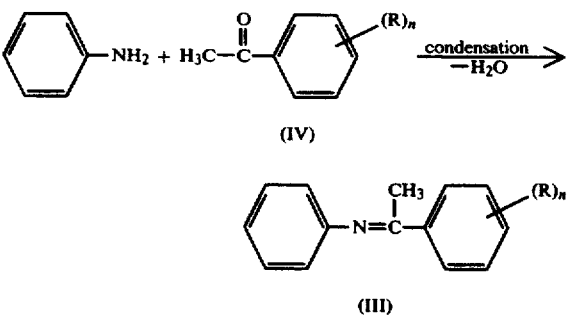

According to the process of this invention, p-nitroaniline can be easily produced in a markedly increased yield of about 99% or more from the α-methylbenzalaniline of formula (III) as schematically shown below.

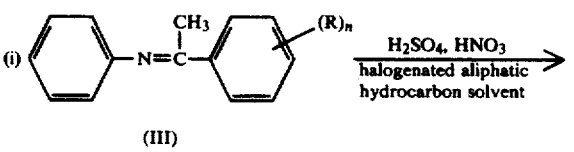

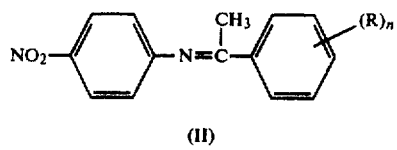

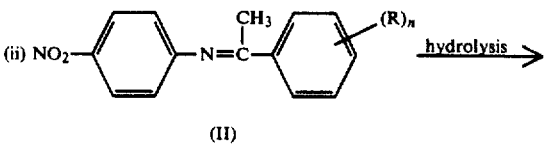

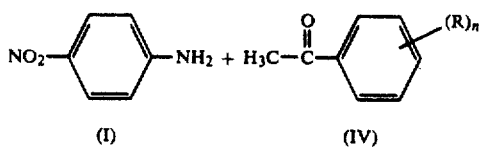

The compound of formula (IV) formed as a by-product in the hydrolysis step (ii) can be recycled for use in the production of the starting compound of formula (III).

The process of this invention is described below in detail including the production of the starting compound of formula (III).

The compound of formula (IV) used in the production of the starting compound of formula (III) includes, for example, acetophenone; methylacetophenones such as o-methylacetophenone, m-methylacetophenone and p-methylacetophenone; ethylacetophenones such as o-ethylacetophenone, m-ethylacetophenone and p-ethylacetophenone; and isopropylacetophenones such as o-isopropylacetophenone, m-isopropylacetophenone and p-isopropylacetophenone.

Acetophenone occurs as a by-product in the production of phenol by the cumene process involving acid cleavage of cumene hydroperoxide. Methylacetophenones occur as a by-product in the process of producing cresol by oxidizing cymene to cymene hydroperoxide followed by acid cleavage. Also, isopropylacetophenones occur as a by-product in the production of dihydroxybenzenes by oxidizing diisopropylbenzene to diisopropylbenzene dihydroperoxide and cleaving it with an acid. Accordingly, the use of acetophenone and these alkylacetophenones is economically advantageous.

The condensation reaction of aniline with the compound of formula (IV) may be carried out by contacting aniline with the compound of formula (IV) in the presence of an acid catalyst. The reaction can be performed at a temperature of, for example, about 30° to about 300° C., preferably about 100° to about 250° C., while removing water formed by the condensation reaction out of the reaction system. The reaction may be carried out in the presence or absence of a solvent. The mole ratio between aniline and the compound of formula (IV) can be properly chosen. For example, about 0.1 to about 10 moles of the compound of formula (IV) can be used per mole of aniline. The amount of a solvent which may be used is, for example, about 0.01 to about 10 times, preferably about 0.05 to about 5 times, the weight of aniline. After the reaction, the starting compound of formula (III) may be separated and recovered by subjecting the reaction mixture to a separating means such as distillation, extraction or crystallization. In the process of this invention, the reaction mixture so obtained may be directly used in the nitrating step.

Examples of the acid catalyst used in the production of the starting compound (IV) include solid acids such as silica, alumina, silica-alumina, zirconia and titania; organic sulfonic acids such as methanesulfonic acid, ethanesulfonic acid, decanesulfonic acid, benzenesulfonic acid and toluenesulfonic acid; organic carboxylic acids such as acetic acid, propionic acid, butyric acid, monochloroacetic acid, dichloroacetic acid, stearic acid, benzoic acid and salicyclic acid; Lewis acids such as zinc chloride, iron chloride and aluminum chloride; and inorganic proton acids such as sulfuric acid, hydrochloric acid and phosphoric acid. These compounds can be used either singly or as a mixture of two or more.

Examples of the solvent which may be used in the production of the starting compound (III) are lower alcohols such as methanol, ethanol, n-propanol, isopropanol and butanol; lower aliphatic carboxylic acids such as acetic acid and propionic acid; and aromatic hydrocarbons such as benzene, toluene, xylene, ethylbenzene, cumene and cymene.

According to the process of this invention, the α-methylbenzalaniline of formula (III) which may, for example, be obtained as above is nitrated with nitric acid in the presence of a halogenated aliphatic hydrocarbon solvent and sulfuric acid to form a p-nitro-α-methylbenzalaniline of formula (II).

An excessive amount of water in the reaction system during the nitration reaction is likely to cause hydrolysis of the compound of formula (III) and tends to increase the amount of a by-product m-nitrated product. Accordingly, the reaction should desirably be carried out under conditions which do not lead to the presence of an excessive amount of water. Concentrated sulfuric acid, for example having a concentration of 95% or more, is desirable as sulfuric acid, and fuming nitric acid, preferably having a concentration of at least 90%, is desirable as nitric acid.

The amount of nitric acid used is, for example, about 0.8 to about 2 moles, preferably about 1 to about 1.5 moles, per mole of the compound of formula (III). The amount of sulfuric acid used is, for example, at least about 2 moles, preferably about 3 to about 20 moles, per mole of the compound of formula (III).

Preferably, the nitration reaction is carried out with stirring. The reaction temperature can be properly selected, and is, for example, about −30° C. to about 50° C., preferably about −20° C. to about 30° C. The reaction is carried out in the presence of a halogenated hydrocarbon solvent. The use of the solvent can inhibit a side-reaction of nitrating the α-methylbenzal group of the starting compound (III), and brings about an improvement in the selectivity of nitration of the p-position, resulting in the production of p-nitroaniline in high yields.

Examples of the halogenated aliphatic hydrocarbons include methylene chloride, chloroform, carbon tetrachloride, ethyl chloride, ethylene dichloride (1,2-dichloroethane), 1,1,2-trichloroethane, 1,1,1-trichloroethane, tetrachloroethane, methyl bromide, ethyl bromide, octyl bromide, and tetrabromoethane. Among these, preferred are chlorinated $C_1$–$C_2$ aliphatic hydrocarbons such as methylene chloride, chloroform, carbon tetrachloride, 1,2-dichloroethane.

The amount of the solvent is, for example, about 0.05 to about 40 times, preferably about 0.1 to about 30 times, the weight of the compound of formula (III).

It is possible to mix a part or the whole of the halogenated aliphatic hydrocarbon solvent with nitric acid, and feed the mixture into the reaction system.

The nitration reaction mixture so obtained may be subjected to a separating means such as distillation or crystallization to separate the compound of formula (III) which can be used in the subsequent hydrolyzing step. Or the nitration reaction mixture may be directly subjected to the hydrolysis treatment. Or the nitration reaction mixture may be used in the hydrolysis step after removing the solvent therefrom.

In the next step of the process of this invention, the p-nitro-α-methylbenzalaniline of formula (II) obtained as above is then hydrolyzed. The hydrolysis can be performed in the presence or absence of a catalyst, preferably in the presence of a catalyst.

Acid catalyst or basic catalysts can be used as the catalyst in the hydrolysis treatment. Examples of the acid catalysts are inorganic proton acids such as sulfuric acid, nitric acid, hydrochloric acid and phosphoric acid; organic proton acids such as methanesulfonic acid, ethanesulfonic acid, decanesulfonic acid, benzenesulfonic acid, toluenesulfonic acid, acetic acid, propionic acid, butyric acid, monochloroacetic acid, dichloroacetic acid, stearic acid, benzoic acid and alicyclic acid; solid acids such as silica, alumina, silica-alumina, zirconia and titania. Examples of the basic catalysts are lithium hydroxide, sodium hydroxide, potassium hydroxide, calcium hydroxide, strontium hydroxide and barium hydroxide. The acid catalyst are preferred, and the inorganic proton acids are especially preferred. Above all, sulfuric acid is preferred.

The nitration reaction mixture mentioned above may be conveniently used as the compound (II) in the hydrolysis step because sulfuric acid contained therein can be utilized as the catalyst for the hydrolysis. Hydrolysis proceeds by adding water to the nitration reaction mixture, and contacting the oil layer with the aqueous layer with stirring. The suitable amount of water used in the hydrolysis is at least about 1 mole per mole of the compound (II), for example about 1 to about 200 moles, per mole of the compound (II). The hydrolysis can be carried out at room temperature, but heating may be done in order to increase the rate of the reaction. For example, temperatures of up to about 70° C. can be used.

By treating the hydrolysis reaction mixture after the hydrolysis by a separating means such as distillation, extraction and crystallization, p-nitroaniline of formula (I) and the acetophenone of formula (IV) can be selectively obtained in high yields. The compound of formula (I) separated and recovered may be recycled to the production of the α-methylbenzalaniline. Since the compound of formula (IV) can be recovered selectively in high yields in the hydrolysis step, it can be effectively recycled. Catalytic hydrogenating reduction of p-nitroaniline obtained by the process of this invention gives p-phenylenediamine in a quantitative yield.

The following Examples specifically illustrate the process of this invention.

EXAMPLE 1

A three-necked flask equipped with a thermometer, a stirrer and a dropping funnel was charged with 3.9 g of α-methylbenzalaniline, 11.0 g of 97% sulfuric acid and 20 ml of methylene chloride as a reaction solvent. While maintaining the temperature of the contents at 0° to 5° C., 1.5 g of fuming nitric acid (specific gravity 1.50) was added dropwise through the dropping funnel, and the mixture was stirred at the same temperature for 1 hour. Water (5 ml) was added to the reaction mixture, and the mixture was stirred at room temperature for 10 minutes. It was then extracted with diethyl ether. The extract was dried over anhydrous magnesium sulfate, and analyzed by gas chromatography. The conversion of the α-methylbenzalaniline, the yield of nitroaniline and the recovery ratio of acetophenone were calculated in accordance with the following equations.

$$\text{Conversion (\%)} = \left(1 - \frac{\text{Amount (moles) of aniline recovered}}{\text{Amount (moles) of } \alpha\text{-methylbenzalaniline charged}}\right) \times 100$$

$$\text{Yield of nitroaniline (\%)} = \frac{\text{Amount (moles) of nitroaniline formed}}{\text{Amount (moles) of } \alpha\text{-methylbenzalaniline charged}} \times 100$$

$$\text{Recovery ratio of acetophenone (\%)} = \frac{\text{Amount (moles) of acetophenone formed}}{\text{Amount (moles) of } \alpha\text{-methylbenzalaniline charged}} \times 100$$

It was found that the conversion of α-methylbenzalaniline was 100%; the yield of p-nitroaniline was 98.1%; the yield of o-nitroaniline was 0.5%; the yield of m-nitroaniline was 1.2%; and the recovery ratio of acetophenone was 94.5%. There were formed 1.3% of nuclearly nitrated products of acetophenone as by-products.

COMPARATIVE EXAMPLE 1

The same reaction as in Example 1 was carried out except that 16.9 g of trifluoromethanesulfonic acid was used instead of 11.0 g of 97% sulfuric acid. The reaction mixture was treated in the same way as in Example 1. It was found that the conversion of α-methylbenzalaniline was 98.3%; the yield of p-nitroaniline was 78.6%; the yield of o-nitroaniline was 0.3%; the yield of m-nitroaniline was 1.3%; and the recovery ratio of acetophenone was 83.5%. There were formed 8.5% of nuclearly nitrated products of acetophenone as by-products.

EXAMPLE 2

The same reaction as in Example 1 was carried out except that 4.2 g of α-methyl-(4-methylbenzal)aniline was used instead of the α-methylbenzalaniline. The reaction mixture was treated and analyzed in the same way as in Example 1. It was found that the conversion of α-methyl-(4-methylbenzal)aniline was 100%; the yield of p-nitroaniline was 98.8%; the yield of o-nitroaniline was 0.3%; the yield of m-nitroaniline was 0.7%; and the recovery ratio of 4-methylacetophenone was 90.8%. There were formed 0.9% of nuclearly nitrated products of 4-methylacetophenone as by-products.

EXAMPLE 3

The same reaction as in Example 1 was carried out except that 4.7 g of α-methyl-(4-isopropylbenzal)aniline was used instead of the α-methylbenzalaniline. The reaction mixture was treated and analyzed in the same way as in Example 1. It was found that the conversion of α-methyl-(4-isopropylbenzal)aniline was 100%; the yield of p-nitroaniline was 98.5%; the yield of o-nitroaniline was 0.2%; the yield of m-nitroaniline was 0.6%; and the recovery ratio of 4-isopropylacetophenone was 89.3%. There were formed 0.9% of nuclearly nitrated products of 4-isopropylacetophenone as by-products.

EXAMPLE 4

The same reaction as in Example 1 was carried out except that the amount of 97% sulfuric acid was changed to 24 g. The reaction mixture was treated and analyzed in the same way as in Example 1. It was found that the conversion of α-methylbenzalaniline was 100%; the yield of p-nitroaniline was 99.3%; the yield of p-nitroaniline was 0.2%; the yield of m-nitroaniline was 0.5%; and the recovery ratio of acetophenone was 92.7%. There were formed 1.9% of nuclearly nitrated products of acetophenone as by-products.

EXAMPLES 5 TO 7

The same reaction as in Example 1 was carried out except that 20 ml of each of the solvents shown in Table 1 was used instead of methylene chloride. The reaction mixture was treated and analyzed in the same way as in Example 1. The results are shown in Table 1.

TABLE 1

| Example | Solvent | Conversion of α-methylbenzalaniline (%) | Yield of nitroanilines (%) | | | Recovery ratio of acetophenone (%) |
|---|---|---|---|---|---|---|
| | | | p- | o- | m- | |
| 5 | 1,2-Dichloroethane | 100 | 96.2 | 0.4 | 0.9 | 95.1 |
| 6 | 1,1,2-Trichloroethane | 97.5 | 94.0 | 0 | 1.3 | 93.1 |
| 7 | 1,1,2,2-Tetrachloroethane | 96.6 | 94.5 | 0 | 1.0 | 91.4 |

EXAMPLE 8

The same reaction as in Example 1 was carried out except that the amount of fuming nitric acid (specific gravity 1.50) was changed to 2.0 g. The reaction mixture was treated and analyzed in the same way as in Example 1. It was found that the conversion of α-methylbenzalaniline was 100%; the yield of p-nitroaniline was 95.8%; the yield of o-nitroaniline was 0.8%; the yield of m-nitroaniline was 1.3%; and the recovery ratio of acetophenone was 90.0%. There were formed 3.6% of nuclearly nitrated products of acetophenone as by-products.

COMPARATIVE EXAMPLE 2

The same reaction as in Example 1 was carried out except that methylene chloride was not used. The reaction mixture was treated and analyzed in the same way as in Example 1. It was found that the conversion of α-methylbenzalaniline was 84.2%; the yield of p-nitroaniline was 76.0%; the yield of o-nitroaniline was 2.0%; the yield of m-nitroaniline was 6.0%; and the recovery ratio of acetophenone was 91.7%. There were formed 7.7% of nuclearly nitrated products of acetophenone as by-products.

What we claim is:

1. A process for producing a p-nitroaniline, which comprises nitrating an α-methylbenzalaniline of the formula

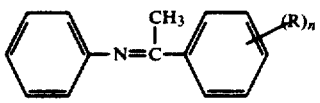

wherein R represents an alkyl group having 1 to 5 carbon atoms, and n is 0 or 1, with nitric acid having a concentration of at least 90% in the presence of a halogenated aliphatic hydrocarbon solvent and concentrated sulfuric acid to form a p-nitro-α-methylbenzalaniline of the formula

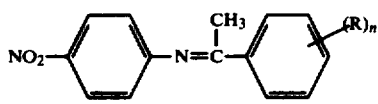

wherein R and n are as defined above, and hydrolyzing the p-nitro-α-methylbenzalaniline.

2. The process of claim 1 wherein the amount of sulfuric acid is about 2 to about 20 moles per mole of the α-methylbenzalaniline.

3. The process of claim 1 wherein the amount of nitric acid is about 0.8 to about 2 moles per mole of the α-methylbenzalaniline.

4. The process of claim 1 wherein the nitration is carried out at a temperature of about −30° C. to about 50° C.

5. The process of claim 1 wherein the hydrolysis is carried out in the presence of an acid catalyst.

6. The process of claim 1 wherein the halogenated aliphatic hydrocarbon solvent is a chlorinated $C_1$–$C_2$ aliphatic hydrocarbon solvent.

7. The process of claim 1 wherein the α-methylbenzalaniline is formed by the condensation reaction between aniline and an acetophenone of the formula

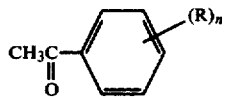

wherein R and n are as defined in claim 1, and wherein the acetophenone formed as a by-product of the hydrolysis of the p-nitro-α-alkylbenzalaniline is recycled to said condensation reaction with aniline.

* * * * *